United States Patent [19]

Gomringer et al.

[11] Patent Number: 5,224,949
[45] Date of Patent: Jul. 6, 1993

[54] CAMMING DEVICE

[75] Inventors: Gary W. Gomringer, La Mesa; Thomas A. Trozera, Del Mar, both of Calif.

[73] Assignee: Interventional Technologies, Inc., San Diego, Calif.

[21] Appl. No.: 820,755

[22] Filed: Jan. 13, 1992

[51] Int. Cl.$^5$ .......................................... A61B 17/32
[52] U.S. Cl. .................................. 606/159; 606/170
[58] Field of Search ............. 606/159, 170, 171, 180, 606/167, 166; 30/151; 604/22, 54

[56] References Cited

U.S. PATENT DOCUMENTS

| | | | |
|---|---|---|---|
| 2,556,783 | 6/1951 | Wallace | 128/321 |
| 2,729,210 | 1/1956 | Spencer | 128/2 |
| 2,730,101 | 1/1956 | Hoffman | 128/305 |
| 2,749,909 | 6/1956 | Ullery et al. | 128/2 |
| 3,320,957 | 5/1967 | Sokolik | 128/311 |
| 3,512,519 | 10/1967 | Hall | 128/2 |
| 3,605,721 | 9/1971 | Hallac | 128/2 B |
| 3,815,604 | 6/1974 | O'Malley et al. | 128/305 |
| 3,990,453 | 11/1976 | Doaves et al. | 128/305 |
| 4,111,207 | 8/1978 | Seiler, Jr. | 128/305 |
| 4,273,128 | 6/1981 | Lary | 128/305 |
| 4,320,762 | 3/1982 | Bentov | 128/343 |
| 4,441,509 | 4/1984 | Kotsifas et al. | 128/757 |
| 4,445,509 | 5/1984 | Auth | 128/305 |
| 4,589,412 | 5/1986 | Kensey | 128/305 |
| 4,598,710 | 7/1986 | Kleinberg | 128/318 |
| 4,603,694 | 8/1986 | Wheeler | 128/312 |
| 4,610,662 | 9/1986 | Weikl et al. | 604/53 |
| 4,627,436 | 12/1986 | Leckrone | 128/303.1 |
| 4,631,052 | 12/1986 | Kensey | 604/22 |
| 4,636,195 | 1/1987 | Wolinsky | 604/53 |
| 4,640,296 | 2/1987 | Schnepp-Pesch et al. | 128/754 |
| 4,646,738 | 3/1987 | Trott | 128/305 |
| 4,650,466 | 3/1987 | Luther | 604/95 |
| 4,653,496 | 3/1987 | Bundy et al. | 128/305 |

(List continued on next page.)

FOREIGN PATENT DOCUMENTS 3732236 12/1988 Fed. Rep. of Germany ...... 606/155

OTHER PUBLICATIONS

Banning G. Lary, M.D., Method for Increasing the Diameter of Long Segments of the coronary Artery, *The American Surgeon*, Jan., 1966. vol. 32. No. 1, pp. 33–35.

Banning G. Lary, M.D., and Roger W. Sherman, M.D., A Method for Creating a Coronary-Myocardial Artery, *Surgery*, St. Louis, Jun. 1966. vol. 59. No. 6, pp. 1061–1064.

Banning G. Lary, M.D., Coronary Artery Incision and Dilation, *Archives of Surgery*, Dec. 1980. vol. 115. pp. 1478–1480.

Primary Examiner—C. Fred Rosenbaum
Assistant Examiner—William Lewis
Attorney, Agent, or Firm—Nydegger & Associates

[57] ABSTRACT

An expandable endarterectomy cutting tool for use in incising plaque at a stenosis in an artery of a patient includes a guide wire, an over-the-wire catheter, and a camming mechanism which is attached near the distal end of the guide wire. The cam mechanism is formed with a plurality of ramps which incline outwardly from the guide wire in a distal direction along the guide wire. A plurality of tethers each have one end attached to the catheter and their other end slidably mounted on one of the ramps in the camming mechanism. A cutting blade is attached to each tether near the end of the tether in the ramp so that as the guide wire is pulled in a proximal direction relative to the catheter, the blades are pushed by the tether up their respective ramp to be radially extended from the cam mechanism. On the other hand, pushing the guide wire in a distal direction relative to the catheter will draw each extended blade back down its respective ramp to retract the blades. In operation, the cam mechanism of the tool is placed distal to the stenosis and the blades are extended. The blades are then drawn across the plaque in the stenosis to weaken the plaque for subsequent dilation of the artery in an angioplasty procedure. The blades are then retracted and the tool is withdrawn from the artery.

14 Claims, 1 Drawing Sheet

U.S. PATENT DOCUMENTS

| | | | |
|---|---|---|---|
| 4,655,217 | 4/1987 | Reed | 128/305 |
| 4,655,771 | 4/1987 | Wallsten | 623/1 |
| 4,664,112 | 5/1987 | Kensey et al. | 128/341 |
| 4,665,918 | 5/1987 | Garza et al. | 128/343 |
| 4,669,469 | 6/1987 | Gifford, III et al. | 128/305 |
| 4,679,557 | 7/1987 | Opie et al. | 128/305 |
| 4,685,458 | 8/1987 | Leckrone | 128/303 |
| 4,686,982 | 8/1987 | Nash | 128/305 |
| 4,690,140 | 9/1987 | Mecca | 128/305 |
| 4,696,667 | 9/1987 | Masch | 604/22 |
| 4,706,671 | 11/1987 | Weinrib | 128/348.1 |
| 4,708,147 | 11/1987 | Haaga | 128/753 |
| 4,728,319 | 3/1988 | Masch | 604/22 |
| 4,732,154 | 3/1988 | Shiber | 128/305 |
| 4,754,755 | 7/1988 | Husted | 128/305 |
| 4,757,826 | 7/1988 | Abdulhay | 128/757 |
| 4,765,332 | 8/1988 | Fischell et al. | 128/305 |
| 4,857,045 | 8/1989 | Rydell | 604/22 |
| 4,887,613 | 12/1989 | Farr et al. | 606/159 |
| 4,895,166 | 1/1990 | Farr et al. | 128/751 |
| 4,950,277 | 8/1990 | Farr | 606/159 |
| 4,966,604 | 10/1990 | Reiss | 606/159 |
| 4,976,723 | 12/1990 | Schad | 606/170 |
| 4,986,807 | 1/1991 | Farr | 604/22 |
| 5,019,088 | 5/1991 | Farr | 606/159 |
| 5,053,044 | 10/1991 | Mueller et al. | 606/170 |

CAMMING DEVICE

FIELD OF THE INVENTION

The present invention pertains to tools which are useful in procedures for clearing plaque obstructions in an artery. More specifically, the present invention pertains to an endarterectomy cutting tool which is useful for incising stenotic tissue in an artery. The present invention is particularly, but not exclusively, useful for weakening plaque in a stenotic segment of an artery to facilitate dilatation of the artery at the stenotic segment during a subsequent angioplasty procedure.

BACKGROUND OF THE INVENTION

Several surgical procedures have been developed in recent years which are intended to clear obstructions from the arteries of a patient so that the normal flow of blood through the patient can be restored. These obstructions, sometimes also referred to as lesions or stenotic segments, can cause very considerable difficulties for the patient. Consequently, they should be removed or cleared at the earliest convenience, if not immediately.

Presently, there are primarily two quite different procedures which are used for clearing an obstruction in an artery. One is an atherectomy procedure wherein the plaque which is causing the obstruction is cut and actually removed from the artery. An example of such a procedure is disclosed in U.S. Pat. No. 4,887,613 for an invention entitled "Cutter for Atherectomy Device" which is assigned to the assignee of the present invention. The other is an angioplasty procedure wherein the plaque is pushed aside by an expanding balloon to dilate the artery. The present invention is more concerned with this later type procedure, i.e. an angioplasty procedure.

As might be expected, the plaque which builds up in an artery to eventually obstruct the flow of blood through the artery can have significantly different consistencies. Sometimes the plaque is relatively soft and can be fairly easily deformed. Plaque of this nature has been likened somewhat to cheddar cheese. In other cases, the plaque can be relatively hard or brittle and can even be somewhat fibrous in nature. In this later case, the plaque is not so easily deformed. Moreover, the plaque in any given stenotic segment will most likely not be homogenous and will include plaque having several different consistencies. The consequence is that it is not uncommon for an obstruction to be, at least partially, composed of the more hard and brittle plaque which is not so easily deformed. Unfortunately, the ability to deform the plaque in an obstruction, and to thereby dilate the artery, is of utmost importance for the efficacy of an angioplasty procedure. Thus, in order to improve the expected results of an angioplasty procedure, and particularly in those cases where the plaque may put up stiff resistance there is a need to properly prepare the obstruction for subsequent dilatation of the artery.

In light of the above, it is an object of the present invention to provide an expandable endarterectomy cutting tool for incising stenotic tissue in an artery which will weaken plaque in a stenotic segment and thereby facilitate a subsequent angioplasty procedure. Another object of the present invention is to provide an expandable endarterectomy cutting tool for incising stenotic tissue in a predictable manner which efficiently promotes dilatation of the stenotic segment. Still another object of the present invention is to provide an expandable endarterectomy cutting tool for incising stenotic tissue in an artery which is safe to use. Another object of the present invention is to provide an expandable endarterectomy cutting tool for incising stenotic tissue in an artery which has a cutting tool that provides positive expansion and contraction of its cutting blades. Yet another object of the present invention is to provide an expandable endarterectomy cutting tool for incising stenotic tissue in an artery which is relative simple to manufacture, easy to use, and comparatively cost effective.

SUMMARY OF THE INVENTION

An expandable endarterectomy cutting tool for incising stenotic tissue includes an over-the-wire catheter which is formed with a lumen. A guide wire having a proximal end and a distal end is slidably disposed in the lumen of the catheter with both the distal end and the proximal end of the guide wire projecting from their respective end of the catheter. A camming mechanism is fixedly attached to the projecting distal end of the guide wire, and an actuator is fixedly attached to the projecting proximal end of the guide wire.

The camming mechanism of the cutting tool is formed with a plurality of ramps which are each aligned along the guide wire, and which are inclined to increase the radial distance of the ramp from the guide wire in the distal direction. A plurality of blades, each having a cutting edge projecting radially outward from the tool are mounted on the camming mechanism for movement up and down the ramps. Specifically, each one of these blades is individually mounted on a tether. Each tether has one end, where the blade is mounted, that is slidingly disposed on one of the ramps of the camming mechanism. The opposite end of each tether is connected directly to the catheter.

The tethers of the cutting tool are basically flat ribbon-shaped members that have a substantially rectangular cross section which resists twisting around a lengthwise axis. Additionally, this configuration resists buckling along the length of the tether, yet it does allow some bending around a width-wise axis. The proximal end of each tether is fixedly attached to the catheter and its associated blade is attached near the distal end of the tether. Each ramp on the camming mechanism is formed with a pair of oppositely disposed grooves which slidingly receive the edges of their associated tether. Thus, the engagement of the grooves with the edges of the tether helps to hold the blade on the camming mechanism and to rigidize the tether.

In the operation of the expandable endarterectomy cutting tool of the present invention, the distal end of the tool is first inserted into the artery and the camming mechanism is positioned distal to the stenotic segment. The actuator is then pulled proximally. This causes the camming mechanism to move proximally toward the catheter, and consequently causes the tethers to push the blades up the ramps of the camming mechanism. As the blades are advanced up the ramps, their cutting edges radially extended from the camming mechanism. The cutting tool is then pulled across the stenotic segment to incise and weaken the plaque on the stenosis to facilitate subsequent dilation of the artery in an angioplasty procedure. Once the incisions have been made, the actuator is pushed distally. This causes the camming mechanism to move distally, and consequently causes the tethers to pull the blades down the ramps of the camming mechanism. As the blades are pulled down the ramps, their cutting edges are retracted back into the camming mechanism. The cutting tool can then be safely withdrawn from the artery of the patient.

The novel features of this invention, as well as the invention itself, both as to its structure and its operation will be best understood from the accompanying drawings, taken in conjunction with the accompanying description, in which similar reference characters refer to similar parts, and in which:

DESCRIPTION OF THE PREFERRED EMBODIMENTS

Figure 1:
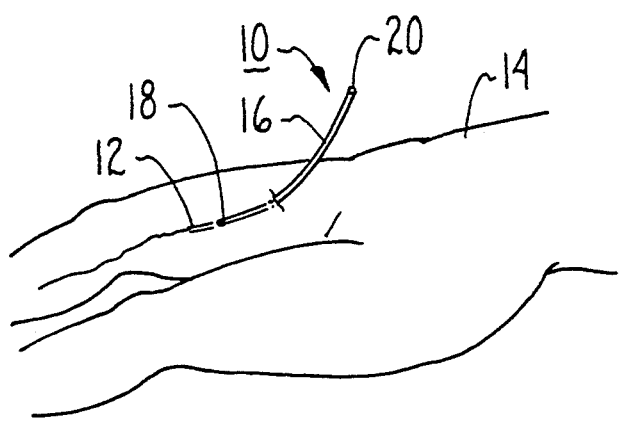
FIG. 1 is a view of a patient with the endarterectomy cutting tool of the present invention inserted into a peripheral artery.

Referring initially to FIGURE an endarterectomy cutting tool in accordance with the present invention in shown and is generally designated 10. Specifically, the cutting tool 10 is shown inserted into a peripheral artery 12 of a patient 14 for the purposes of incising a stenotic segment in the artery 12. In turn, the purpose of the incision is to weaken the stenotic segment and thereby facilitate a subsequent angioplasty operation for dilatation of the stenotic segment in the artery 12. FIG. 1 also shows that the endarterectomy cutting tool 10 of the present invention includes a catheter 16, a camming mechanism 18 and an actuator 20. For purposes of the present invention, the catheter 16 can be made of a composite material well known in the pertinent art which is useful for the manufacture of a medical catheter. Just how these components interact with each other and with other components of the cutting tool 10 will be better appreciated with reference to FIG. 2.

Figure 2:
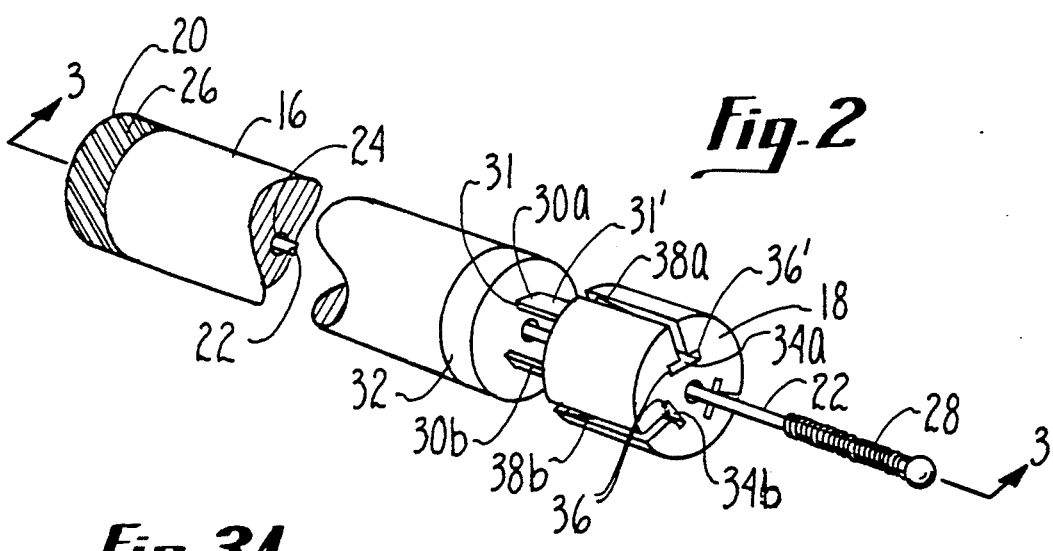
FIG. 2 is a perspective view of the endarterectomy cutting tool of the present invention.

In FIG. 2 it will be seen that the cutting tool 10 of the present invention includes a guide wire 22. Additionally, beginning at the proximal end of the cutting tool 10 and proceeding distally, it is to be understood that the actuator 20 is fixedly attached to the proximal end of the guide wire 22. As shown, the actuator 20 has a textured surface 26 which facilitates the grasping and manipulation of the actuator 26. Next, the catheter 16 is formed with a lumen 24 for receiving the guide wire 22 therethrough. Thus, catheter 16 is an over-the-wire catheter which is slidingly positioned on the guide wire 22. Like the actuator 20, but unlike the catheter 16, the camming mechanism 18 is fixedly attached to the guide wire 22. The extreme distal end of the guide wire 22 includes a flexible radiopaque coil 28 which helps steer the tool 10 into the artery 12 of the patient 14 and which can be used under fluoroscopy to locate the exact position of the tool 10 in the patient 14.

Figure 3A:
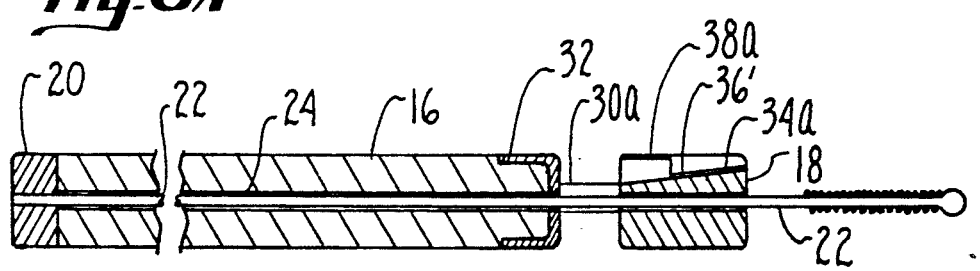
FIG. 3A is a cross sectional view of the endarterectomy cutting tool of the present invention as seen along the line 3—3 in FIG. 2 with the tool in its first configuration wherein the camming mechanism is distanced from the catheter.
Figure 3B:
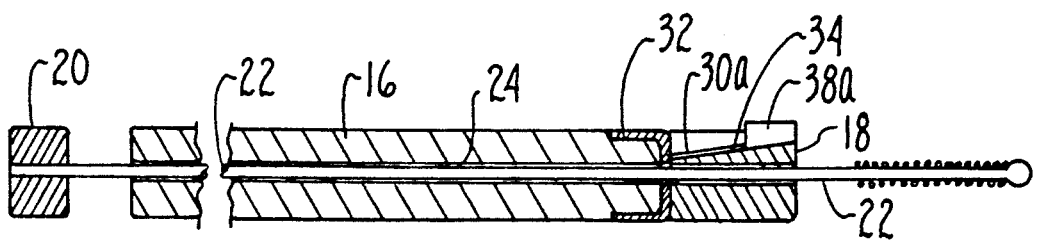
FIG. 3B is a cross sectional view of the endarterectomy cutting tool of the present invention as seen along the line 3—3 in FIG. 2 with the tool in its second configuration wherein the camming mechanism abuts the catheter.

As perhaps best appreciated by cross referencing FIG. 2 with FIGS. 3A and 3B, the cutting tool 10 includes a plurality of tethers 30. Each tether 30 is a substantially flat ribbon-shaped structure having an side 31 and another side 31' opposite thereto. The FIGURES also show that the camming mechanism 18 is formed with a plurality of ramps 34, of which ramps 34a and 34b are representative, and that each ramp is formed with a pair of opposed grooves 36 and 36'. As intended for the present invention, the sides 31 and 31' of the distal end of each tether 30 are slidingly engaged with the grooves 36 and 36' of a respective ramp 34 on the camming mechanism 18. Thus, the tethers 30 are slidingly disposed on the camming mechanism 18. For purposes of the present invention, the ramps 34 are inclined relative to the guide wire 34 so that their radial distance from the guide wire 34 is increased along the ramp when moving in a distal direction. Preferably, the slope of the ramps 34 is approximately seven degrees (7°) measured relative to the guide wire 22.

A cutting blade 38 is mounted on the distal end of each tether 30, substantially as shown. Consequently, the blade 38 is moveable with the tether 30. For example, tether 30a is fixedly attached to the end cap 32 on catheter 16 and is, therefore, moveable with the catheter 16. On the other hand, with its sides 31 and 31' positioned respectively in the grooves 36 and 36', the tether 30a is slidingly disposed on ramp 34a of camming mechanism 18. With this structure, the blade 38a is set to move with the distal end of the tether 30a. The same structure and consequent movement applies to the other tethers 30, and their associated blades 38. Further, although only three blades 38 are shown in the FIGURES, it is to be understood that the number of blades 38 which are employed with the endarterectomy cutting tool 10 of the present invention is a matter of design preference.

In the operation of the endarterectomy cutting tool 10 of the present invention, the tool 10 is manipulable between a first configuration (shown in FIG. 3A) and a second configuration (shown in FIG. 3B). Initially, tool 10 is placed into its first configuration as shown in FIG. 3A. With this configuration it will be seen that the catheter 16 is positioned proximally on the guide wire 22 with the catheter 16 abutting the actuator 20. Also, the blades 38 are positioned at the lower proximal end of the ramp 34 and are thus retracted into the camming mechanism 18. For comparison, this first configuration for cutting tool 10 is also the configuration shown for the tool 10 in FIG. 2. In any event, it is while the endarterectomy cutting tool 10 is in its first configuration that the tool 10 is initially inserted into the artery 12 of the patient 14.

Once the tool 10 is positioned in a artery 12 of the patient 14, as desired by the operator, the tool 10 is manipulated into its second configuration shown in FIGURE 3B. To make this transition, the operator merely grasps the actuator 20 and moves the catheter 16 therefrom in a distal direction. Stated differently, the catheter 16 is held stationary and the actuator 20 is pulled proximally therefrom. In either case, the important change is that the movement of catheter 16 along guide wire 22 forces the tether 30 and its attached blade 38 up the respective ramp 34 of camming mechanism 18. Recall that the camming mechanism 18 is fixedly attached to the guide wire 22. This movement causes the blade 38 to be extended from the camming mechanism 18, in a manner as shown in FIG. 3B, and exposes the blade 38.

With the blades 38 exposed and extended from the camming mechanism 18, as shown for the second configuration in FIG. 3B, the operator can then move the cutting tool 10 back and forth across any lesion or stenotic segment in the artery 12. The blades 38 thus incise the plaque which is causing the lesion, and thereby weaken it for a subsequent angioplasty operation. Importantly, the cutting tool 10 is maintained in its second configuration while the incisions are being made.

After the work with endarterectomy cutting tool 10 is completed, the actuator 20 is again manipulated to return the tool 10 to its first configuration shown in FIG. 3A. This, consequently, retracts the blades 38 into the camming mechanism 18 and allows the tool 10 to be withdrawn from the patient 14 without further cutting of tissue.

We claim:

1. An expandable endarterectomy cutting tool for incising stenotic tissue in an artery of a patient which comprises:

a camming mechanism formed with a ramp;
means for slidably supporting a blade on said ramp;
means for positioning said camming mechanism in said artery, said positioning means further comprising a catheter formed with a lumen and a guide wire slidably disposed in said lumen with a distal end projecting from said catheter and a proximal end projecting from said catheter;
means for holding said blade to said positioning means; and
means for moving said camming mechanism relative to said positioning means to slide said blade up and down said ramp to respectively extend and retract said blade, said blade being extended to incise said stenotic tissue and retracted to insert said tool into said artery and to remove said tool from said artery.

2. A tool as recited in claim 1 wherein said camming mechanism is fixedly attached to said distal end of said guide wire, and said ramp formed on said camming mechanism increases in radial distance from said guide wire in a direction from proximal to distal.

3. A tool as recited in claim 2 wherein said holding means is a tether, and said tether is a substantially flat member having a rectangular cross section defining both a top surface and a bottom surface extending from a proximal end to a distal end with sides therebetween.

4. A tool as recited in claim 3 wherein said moving means is an actuator fixedly attached to said proximal end of said guide wire, said actuator being manipulable to pull said camming mechanism in a proximal direction and move said blade up said ramp to radially extend said blade, and to push said camming mechanism in a distal direction and move said blade down said ramp to radially retract said blade.

5. A tool as recited in claim 4 further comprising a plurality of said blades, and wherein said camming mechanism is formed with a plurality of said ramps, each said blade being slidably supported in one said ramp.

6. A tool as recited in claim 5 wherein each said ramp of said camming mechanism is formed with a pair of oppositely disposed grooves, and wherein each said blade is mounted on one said tether with said sides of said tether establishing lateral extensions individually engageable with one of said grooves for holding said blade on said camming mechanism.

7. A tool as recited in claim 6 wherein each said blade has a cutting edge extending radially from said guide wire.

8. A tool as recited in claim 7 wherein said ramp has an incline of approximately seven degrees (7°).

9. An expandable endarterectomy cutting tool for incising stenotic tissue in an artery of a patient which comprises:

tether formed with a lumen;
a guide wire slidably disposed in said lumen, said guide wire having a distal end projecting from said catheter and having a proximal end projecting from said catheter;
a camming mechanism fixedly attached to said distal end of said guide wire, said camming mechanism being formed with a ramp, with said ramp increasing distally in radial distance from said guide wire;
a blade slidingly disposed on said ramp; and
a tether connecting said blade to said catheter.

10. A tool as recited in claim 5 further comprising an actuator fixedly attached to said proximal end of said guide wire for moving said cam actuator proximally to move said blade up said ramp to radially extend said blade and for moving said cam actuator distally to move said blade down said ramp to radially retract said blade.

11. A tool as recited in claim 10 wherein said tether is a substantially flat member having a rectangular cross section defining a top surface and a bottom surface, both said top and bottom surfaces extending from a proximal end to a distal end with sides therebetween, and wherein said ramp of said cam mechanism is formed with a pair of oppositely disposed grooves, and further wherein said blade is mounted on said tether with said sides of said tether establishing lateral extensions individually engageable with one of said grooves for holding said blade on said camming mechanism.

12. A tool as recited in claim 11 further comprising a plurality of said blades and a plurality of said tethers, and wherein said cam mechanism is formed with a plurality of said ramps, each said blade being mounted on one said tether and slidably supported in one said ramp.

13. A tool as recited in claim 12 wherein each said blade has a cutting edge extending radially from said guide wire and said ramp has an incline of approximately seven degrees (7°).

14. A method for incising stenotic tissue in an artery of a patient which comprises the steps of:

inserting a cutting tool into said artery, said tool comprising a catheter formed with a lumen; a guide wire slidably disposed in said lumen, said guide wire having a distal end projecting from said catheter and having a proximal end projecting from said catheter; a camming mechanism fixedly attached to said distal end of said guide wire, said camming mechanism being formed with a ramp, with said ramp increasing distally in radial distance from said guide wire; a blade mounted on a tether and slidingly disposed on said ramp with said tether connecting said blade to said catheter; and an actuator fixedly attached to said proximal end of said guide wire for moving said cam actuator proximally to move said blade up said ramp to radially extend said blade and for moving said cam actuator distally to move said blade down said ramp to radially retract said blade;

positioning said tool with said camming mechanism distally to said stenotic tissue;
pulling said actuator proximally to move said blade up said ramp to radially extend said blade;
simultaneously pulling said catheter and said actuator to draw said extended blade across said stenotic tissue to incise said tissue;
pushing said actuator distally to move said blade down said ramp to radially retract said blade; and
withdrawing said tool from said artery.

* * * * *

UNITED STATES PATENT AND TRADEMARK OFFICE
CERTIFICATE OF CORRECTION

PATENT NO. : 5,224,949

DATED : July 6, 1993

INVENTOR(S) : Gary W. Gomringer and Thomas A. Trozera

It is certified that error appears in the above-identified patent and that said Letters Patent is hereby corrected as shown below:

In claim 9, on col. 6 at line 11, the word "tether" should be deleted and the words -- a catheter -- inserted therefor.

Signed and Sealed this

Eighteenth Day of January, 1994

Attest:

BRUCE LEHMAN

Attesting Officer

Commissioner of Patents and Trademarks